United States Patent [19]

Dietz et al.

[11] Patent Number: 4,620,145
[45] Date of Patent: Oct. 28, 1986

[54] NON-DESTRUCTIVE DETECTION OF VOIDS IN PLASTIC MATERIALS

[75] Inventors: Peter W. Dietz, Greenwich; Amandus H. Sharbaugh, Clifton Knolls, both of N.Y.

[73] Assignee: General Electric Company, Schenectady, N.Y.

[21] Appl. No.: 642,227

[22] Filed: Aug. 20, 1984

[51] Int. Cl.$^4$ .................... G01N 27/61; G01N 27/62; G01N 27/42
[52] U.S. Cl. ........................................ 324/54; 324/72; 324/456
[58] Field of Search ............ 324/456, 457, 72, 123 R, 324/54, 51

[56] References Cited

U.S. PATENT DOCUMENTS 4,259,666 3/1981 Takahashi ............................. 324/72
4,262,254 4/1981 Poss ..................................... 324/72

FOREIGN PATENT DOCUMENTS 2814064 6/1979 Fed. Rep. of Germany ...... 324/456
7914466 1/1981 France ................................ 324/456
2034898 6/1980 United Kingdom ............... 324/456

*Primary Examiner*—Reinhard J. Eisenzopf
*Assistant Examiner*—Jose M. Solis
*Attorney, Agent, or Firm*—Richard V. Burgujian; James C. Davis, Jr.; Paul R. Webb, II

[57] ABSTRACT

A sensitive yet non-destructive method and apparatus for detecting the presence of voids contained within dielectric materials is disclosed which comprises applying a voltage across the dielectric material to create an electric field therethrough, increasing this voltage to create a partial electrical discharge and monitoring the field current to detect the voltage at which partial discharge occurs. When the partial discharge is detected, the voltage applied across the test material is recorded. Reference can then be made to mathematical charts and formulas readily available to determine the size and shape of the detected void.

8 Claims, 1 Drawing Figure

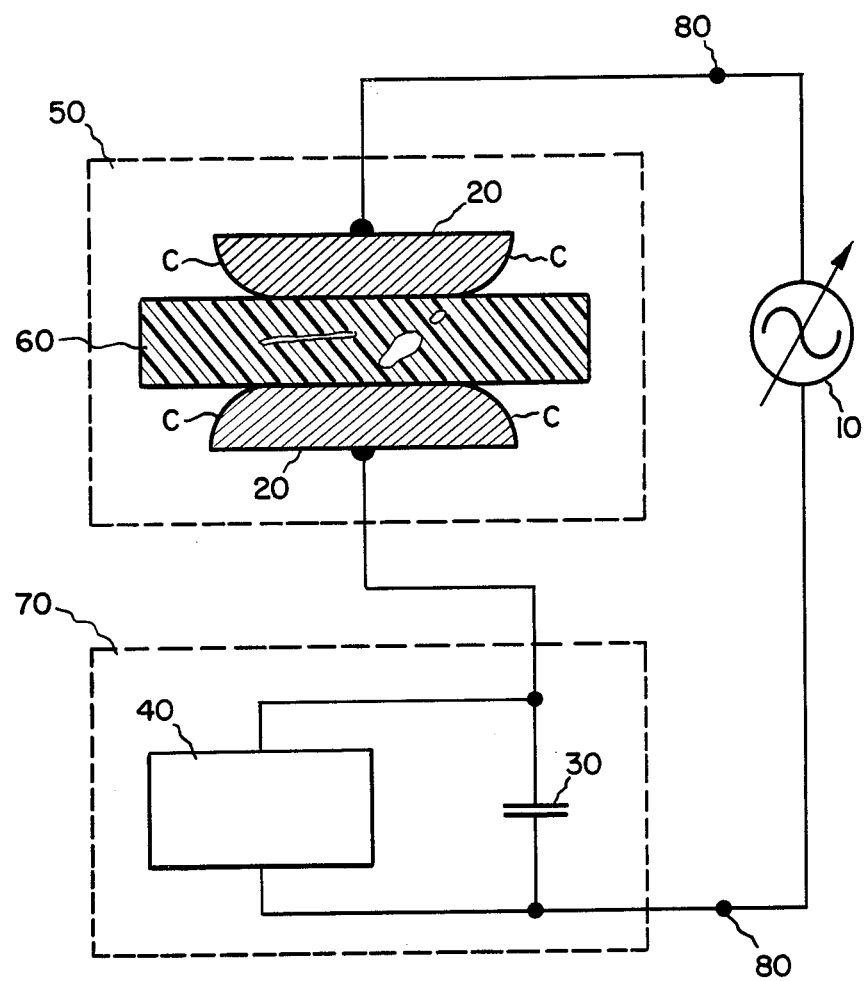

NON-DESTRUCTIVE DETECTION OF VOIDS IN PLASTIC MATERIALS

BACKGROUND OF THE INVENTION

This invention is directed in general to a method for determining the characteristics of a dielectric material and, more particularly, to a non-destructive, yet sensitive, method and apparatus for detecting the presence or absence of voids contained internally of a plastic material.

Specifically, apparatus is provided to create an alternating electric field through the dielectric material and to increase the strength of this field to create a partial electrical discharge. The field is constantly monitored to detect this partial discharge. As used herein, partial electrical discharge refers to the incipient stages of dielectric breakdown characterized by the transfer of small amounts of electrical charge through a gaseous inclusion, or void, within the dielectric. This transfer of charge through the gaseous inclusion modifies the charge distribution within the dielectric, thus instantaneously altering the magnitude of the electric field through the dielectric material. Although other charge transfer quickly compensates for this change in field magnitude, the instantaneous decrease thereof, corresponding to the transfer of charge through a gaseous inclusion, can be detected by several well-known methods.

It is known in the art of dielectric breakdown that partial discharge occurs within a void contained internally of dielectric material at an electric field magnitude significantly below that magnitude required for electrical breakdown of the dielectric. It is further known, that the magnitude of the applied field required to cause partial discharge within a void is dependent upon the size and shape of the void, the molecular composition of the gaseous substance contained in the void (usually air but not necessarily so), the pressure and temperature (i.e. density) of the gaseous substance, and the frequency of the applied field. Where all other factors are known and held constant, the size of the gaseous inclusion can be determined by the magnitude of the applied electric field required to cause partial electrical discharge. See, e.g., *Progress in Dielectrics*, Vol. 2, Wiley publishers (1959); See also, *Plastics for Electrical Insulation*, Interscience publishers (1968).

Measurements such as these, to determine the relative size and population of voids within plastic articles without destroying the article, are desirable throughout all areas of plastic manufacture as a relative indication of plastic integrity, quality, uniformity, goodness and strength.

In many plastic applications it is desirable to know the strength of plastic materials to within established limits. Since the strength of plastic material is in large measure determined by its homogeneity, or lack of gaseous voids, a method to directly determine the relative size and population of these voids is obviously desirable.

Further, by including such a process in the manufacture of plastic materials at a point where the plastic material has been produced but has not been formed for a specific application, relative strength of this material can be indirectly determined such that relatively weak materials can be allocated to those applications requiring less strength, and conversely, relatively strong materials can be allocated to those applications requiring higher strength.

Further, in many applications it is desirable for one reason or another to create plastic materials containing voids. Here goodness of plastic material is determined by a uniform population of voids as opposed to a relatively homogenous plastic article. In such applications, a direct measurement of relative population of gaseous inclusions can be made, thereby directly determining the goodness of this article.

As always, there is a need to minimize expense in product testing and to reduce manufacturing costs such that valuable natural resources can be conserved while allowing quality products to be supplied at a lower cost to the consumer.

OBJECTS OF THE INVENTION

Accordingly, it is the principal object of the invention to provide a nondestructive, yet sensitive, method and apparatus for determining the presence or absence of voids contained within a plastic material.

A further object is the provision of an accurate measurement process and apparatus which allows for sensitive testing of plastic materials without destruction thereof.

A still further object is to provide method and apparatus which allows for an inexpensive, yet accurate and sensitive determination of relative integrity of plastic materials.

Further objects and advantages of the present invention will become apparent upon reading of this specification in conjunction with the drawing.

SUMMARY OF THE INVENTION

The above noted and other objects of the invention are accomplished by providing method and apparatus for determining the relative population and size of gaseous inclusions contained internally of dielectric materials by applying an alternating electric field through these materials and increasing the magnitude of this field to detect that magnitude at which partial electrical discharge occurs. To obtain reproducible measurements, the frequency of the applied field and the temperature of the dielectric material should be held constant. The magnitude of electric field at which partial discharge occurs is used to determine the relative size of the detected void by reference to characteristic curves and/or mathematical formulas readily available.

BRIEF DESCRIPTION OF THE DRAWING FIGURE

The invention, both as to organization and method of practice, may best be understood by reference to the drawing in which an illustrative block diagram of the apparatus for carrying out the method of the subject invention is provided.

DETAILED DESCRIPTION OF THE INVENTION

As mentioned hereinbefore, a need exists for accurate, sensitive, sensors to measure the homogeneity of dielectric materials. The present invention is thus provided to determine the relative size and population of gaseous inclusions by applying an alternating electric field through the dielectric material, increasing the magnitude of this electric field and monitoring the resultant electric current to determine the magnitude at which partial electrical discharge occurs.

With reference to the drawing figure, there is shown a pair of field forming electrodes 20 for producing an electric field through the dielectric test material 60. The electrodes 20 are coupled to a variable source of electrical power 10 via conductors 80. Although the magnitude of voltage required to be supplied to electrodes 20 from source 10 to create partial discharge within the plastic material 60 is greatly dependent upon the thickness of the test material, voltage amplitudes less than 50 Kv, and typically approximately 1-10 Kv, at a frequency of 60 Hz should be sufficient for most applications.

The sensitivity of the measurement is affected by the ability to provide a substantially uniform electric field. Where the field is uniform, the field magnitude at which partial discharge occurs will be directly related to the voltage across the field forming electrodes. The magnitude of electric field required for discharge can then be determined from the voltage at which partial discharge occurs. Therefore, electrodes 20 are shown to have gently sloping, contoured, confronting edges C, known within the art to provide a uniform electric field by preventing undesirable discharges at sharp electrode edges.

Further, the accuracy of the subject measurement is affected by the ability to direct the electric field primarily through the test dielectric. This is necessary to assure that discharge occurs through a gas included within the test material as opposed to that occurring through a gas about the periphery of the dielectric, hereinafter referred to as fringe discharge. Hence, electrodes 20 are shown to be of size substantially less than the test dielectric 60 to prevent substantial increase in electric field about the periphery of the test dielectric, thus preventing fringe discharge. Also, immersion of the system in a dielectric liquid or gas of high electric strength is often done to further eliminate undesirable fringe discharge. Thus, in an alternative embodiment container 50, shown in phantom, is provided to contain a fluid which is selected to direct the electric field substantially through the dielectric material thereby preventing fringe discharge. In this embodiment container 50 would be filled with gas of high dielectric strength such as sulfur hexafluoride ($SF_6$), which is known to require an electric field for discharge of approximately twice that required for discharge through air. Insulating oil, which requires even higher discharge inception field, may also be used.

Detector 70 is provided to detect the partial electrical discharge. Although detector 70 is shown in serial relationship with electrodes 20 and source 10, other embodiments and configurations may be possible to achieve the purpose of detecting partial discharge.

Detector 70 is shown to comprise an impedance in the form of capacitor 30 coupled in parallel relationship with a voltage sensor 40. During partial discharge, the instantaneous decrease in voltage between electrodes 20 causes a corresponding increase in the voltage of capacitor 30. Sensing means 40 is provided to detect this instantaneous increase in voltage across capacitor 30.

As shown, sensor 40 comprises a partial discharge detector like that commercially available from the James G. Biddle Co. These detectors are voltage sensitive devices developed for the specific application of detecting partial electrical discharge, and are therefore particularly suited for use with the present invention. However, it will be apparent to one skilled in the art that other voltage sensitive devices capable of detecting an instantaneous voltage change on the order of one picovolt across capacitor 30 may readily be substituted for partial detector 40 without departing from the true spirit and scope of this invention.

In the preferred embodiment, capacitance 30 is selected to have a capacitance within the range of 100 to 1000 pf. It will, however, be readily appreciated by one skilled in the art that other appropriate types of impedance may be substituted for capacitor 30 so long as a measurable electrical charge thereacross is created in response to partial discharge through a void contained within the plastic material 60.

In operation, source 10 is coupled to conductors 80 to energize the circuit by supplying a voltage on the order of 1-10 Kv at a frequency of 60 Hz. The voltage of capacitor 30 is monitored for instantaneous increases corresponding to instantaneous decreases in the voltage across electrodes 20 indicative of partial discharge.

The source voltage is increased in magnitude until partial discharge occurs, the voltage at which it occurs being noted. Reference can then be made to charts and mathematical formulas to determine the size and shape of the void through which the discharge occurred. Continued increase of the electric field past the magnitude at which partial discharge is first detected is to be discouraged, as continued discharge through the voids contained internally of the dielectric material will lead to breakdown of the dielectric. In no event should the applied voltage be raised above the critical level at which the dielectric itself, free of voids, will breakdown. Typically, the critical level is on the order of several hundred kilovolts per inch of thickness. Source voltages approaching this critical level without discharge indicate that no voids are present within the dielectric.

Measurements made in accordance with the method and apparatus described hereinabove can detect a void having a thickness greater than approximately $10^{-3}$ cm in the direction perpendicular to the length of the electrodes. To detect such a void in a typical dielectric sample having a thickness of $10^{-2}$ cm and a dielectric constant of 2, an applied voltage of less than 1 Kv should be sufficient to cause partial discharge. For voids of larger size, partial discharge will occur at higher voltages.

From the above, it is apparent that although the invention has been described with respect to certain specific embodiments and preferred illustrations, it is evident that many modifications and changes may be made without departing from the spirit of the invention. Likewise, while the invention has been described with reference to voids contained within a dielectric, it will be appreciated that the presence of cracks and other discontinuities occurring at the surface or internally of the test material can be detected using this method. Although dielectric materials have been referred to and exemplified herein as plastics, it is apparent that the method and apparatus herein disclosed can be used to detect voids in other dielectric materials, e.g. ceramics, glass, rubber, etc. Accordingly, by the appended claims, we intend to cover all such modifications and changes as fall within the true spirit and scope of this invention.

What we claim is:

1. Apparatus for detecting the presence of a void contained internally of a dielectric material, comprising:
   means for producing an electric field through said material, said field producing means comprising a pair of electrodes disposed to receive said material therebetween and adapted to provide a substantially uniform electric field through said material, said electrode pair being coupled to a source of AC voltage;

means for increasing said field to a level sufficient to cause a partial discharge through said void but insufficient to cause an electrical discharge through said dielectric material, said field increasing means being adapted to increase the magnitude of the voltage applied to said electrode pair, said discharge being characterized by a transfer of a small amount of electrical charge through a gaseous inclusion in said dielectric material; and means for detecting the discharge through said void.

2. Apparatus as recited in claim 1 further comprising means for varying the magnitude of said field between zero and a first value, said first value being less than that necessary for breakdown of the plastic material.

3. A process for detecting voids contained internally of a dielectric material comprising the steps of:

applying an electric field through said material by positioning said material between a pair of electrodes disposed to receive said material therebetween, said electrode pair being coupled to a variable source of AC voltage and adapted to provide substantially uniform electric field through said material;

increasing the magnitude of said field to a predetermined magnitude chosen to be less than that required for corona discharge, said field magnitude being increased by increasing the magnitude of the voltage applied to said electrode pair; and monitoring said field to detect the onset of a partial electrical discharge therethrough, said discharge being characterized by a transfer of a small amount of electrical charge through a gaseous inclusion in said dielectric material, whereby detection of onset corresponds to the presence of a void within said material.

4. Apparatus as recited in claim 1 wherein said detecting means comprises an electrical impedance means coupled in parallel with a voltage sensing means, said detecting means being serially coupled to said field producing means.

5. Apparatus as recited in claim 4 wherein said impedance means comprises a capacitor.

6. Apparatus as recited in claim 4 wherein said voltage sensing means comprises a partial discharge detector for detecting instantaneous increases in the voltage of said impedance means which occur in response to a partial discharge through a void contained in said dielectric.

7. Apparatus as recited in claim 1 further comprising means for substantially reducing fringe discharge.

8. Apparatus as recited in claim 7 wherein said means for reducing fringe discharge comprises container means adapted to contain a fluid, said fluid being chosen to have a high dielectric strength such that it reduces to a minimum the strength of the electric field therethrough and thereby directs said field substantially through said dielectric.

* * * * *